US00PP21600P2

(12) United States Plant Patent
Bullis

(10) Patent No.: US PP21,600 P2
(45) Date of Patent: Dec. 28, 2010

(54) ***NEOREGELIA* PLANT NAMED 'AUTUMN RAIN'**

(50) Latin Name: ***Neoregelia carolinae*×*Neoregelia princeps***
Varietal Denomination: Autumn Rain

(75) Inventor: Patricia E. Gomez Bullis, Princeton, FL (US)

(73) Assignee: Ballis Bromeliads, Princeton, FL (US)

( * ) Notice: Subject to any disclaimer, the term of this patent is extended or adjusted under 35 U.S.C. 154(b) by 0 days.

(21) Appl. No.: 12/462,523

(22) Filed: Aug. 5, 2009

(51) Int. Cl.
*A01H 5/00* (2006.01)

(52) U.S. Cl. ..... Plt./370

(58) Field of Classification Search ..... Plt./370
See application file for complete search history.

*Primary Examiner*—June Hwu
(74) *Attorney, Agent, or Firm*—C. A. Whealy

(57) ABSTRACT

A new and distinct cultivar of *Neoregelia* plant named 'Autumn Rain', characterized by its upright and outwardly arching growth habit; developing leaves of vegetative plants are green and white bi-colored becoming solid pink purple with development; and good interiorscape and landscape performance.

2 Drawing Sheets

Botanical designation: *Neoregelia carolinae* ×*Neoregelia princeps.*

Cultivar denomination: 'Autumn Rain'.

BACKGROUND OF THE INVENTION

The present invention relates to a new and distinct cultivar of *Neoregelia* plant, botanically known as *Neoregelia hybrida* and hereinafter referred to by the name 'Autumn Rain'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2002 in Princeton, Fla. of an unnamed proprietary selection of *Neoregelia carolinae variegata*, not patented, as the female, or seed, parent with an unnamed proprietary selection of *Neoregelia princeps*, not patented, as the male, or pollen, parent. The new Neoregelia plant was discovered and selected by the Inventor as a single plant within the progeny of the stated cross-pollination in a controlled greenhouse environment in Princeton, Fla. in 2002.

Asexual reproduction of the new Neoregelia plant by offsets in a controlled environment in Princeton, Fla. since 2002, has shown that the unique features of this new *Neoregelia* plant are stable and reproduced true to type in successive generations.

SUMMARY OF THE INVENTION

Plants of the new *Neoregelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Autumn Rain'. These characteristics in combination distinguish 'Autumn Rain' as a new and distinct cultivar of *Neoregelia:*

1. Upright and outwardly arching growth habit.
2. Developing leaves of vegetative plants are green and white bi-colored becoming solid pink purple with development.
3. Good interiorscape and landscape performance.

Plants of the new *Neoregelia* differ from plants of the female parent selection in the following characteristics:

1. Plants of the new *Neoregelia* have stronger root systems than plants of the female parent selection.
2. Plants of the new *Neoregelia* have shorter and broader leaves than plants of the female parent selection.
3. Developing leaves of vegetative plants of the new *Neoregelia* have white-colored margins and green-colored centers whereas developing leaves of vegetative plants of the female parent selection have green-colored margins and white-colored centers.

Plants of the new *Neoregelia* differ from plants of the male parent, selection, in the following characteristics:

1. Developing leaves of vegetative plants are green and white bi-colored whereas developing leaves of vegetative plants of the male parent selection are green in color.
2. Plants of the new *Neoregelia* flower earlier than plants of the male parent selection.

Plants of the new *Neoregelia* can be compared to plants of the *Neoregelia* 'Tangerine', not patented. Plants of the new *Neoregelia* and 'Tangerine' differ primarily in leaf color and leaf pattern.

BRIEF DESCRIPTION OF THE PHOTOGRAPHS

The accompanying colored photographs illustrate the overall appearance of the new *Neoregelia* plant, showing the colors as true as it is reasonably possible to obtain in colored reproductions of this type. Colors in the photographs may differ slightly from the color values cited in the detailed botanical description which accurately describe the colors of the new *Neoregelia.*

The photograph at the bottom of the first sheet is a side perspective view of a typical vegetative plant of 'Autumn Rain' grown in a container.

The photograph at the top of the first sheet is a top perspective view of a typical vegetative plant of 'Autumn Rain'.

The photograph at the bottom of the second sheet is a side perspective view of a typical flowering plant of 'Autumn Rain' grown in a container.

The photograph at the top of the second sheet is a top perspective view of a typical flowering plant of 'Autumn Rain'.

DETAILED BOTANICAL DESCRIPTION

The aforementioned photographs and following observations, measurements and values describe plants grown in 15-cm containers in Princeton, Fla. during the spring under commercial practice in a polypropylene-covered shade house with day temperatures ranging from 10° C. to 32° C., night temperatures ranging from 7° C. to 29° C. and light levels averaging 3,200 foot-candles. Single plants used for the photographs and description were 18 months old. In the following description, color references are made to The Royal Horticultural Society Colour Chart, 2007 Edition, except where general terms of ordinary dictionary significance are used.

Botanical classification: *Neoregelia carolinae*×*Neoregelia princeps* 'Autumn Rain'.

Parentage:

*Female, or seed, parent.*—Unnamed proprietary selection of *Neoregelia carolinae*, not patented.

*Male, or pollen, parent.*—Unnamed proprietary selection of *Neoregelia princeps*, not patented.

Propagation:

*Type.*—By offsets.

*Time to initiate roots, summer.*—About 30 days at 30° C. to 32° C.

*Time to initiate roots, winter.*—About 45 days at 30° C. to 32° C.

*Time to produce a rooted young plant, summer.*—About three to four months at 30° C. to 32° C.

*Time to produce a rooted young plant, winter.*—About three to four months at 18° C. to 22° C.

*Root description.*—Medium in thickness, fibrous; yellow to tan in color.

*Rooting habit*—Moderately freely branching; medium density.

Plant description:

*Plant form/growth habit.*—Upright and outwardly arching growth habit; rosette leaves are erect when young, becoming outwardly arching with development; plants readily produce uniform offsets; vigorous growth habit.

*Plant height, vegetative plants.*—About 20 cm.

*Plant height, flowering plants.*—About 13 cm.

*Plant diameter or spread, vegetative plants.*—About 48 cm.

*Plant diameter or spread, flowering plants.*—About 42 cm.

*Internode length, vegetative and flowering plants.*—About 5 mm.

Foliage description:

*Arrangement.*—Rosette, spiral phyllotaxis; simple; sessile, clasping.

*Shape.*—Oblong to ensiform.

*Apex.*—Cuspidate.

*Base.*—Truncate.

*Margin.*—Serrate, spinose.

*Length.*—About 23 cm.

*Width.*—About 5 cm.

*Texture.*—Smooth, glabrous; leathery.

*Venation pattern.*—Parallel.

*Color.*—Lower leaves, vegetative and flowering plants upper surface: Towards the margins, close to 158A; centers, close to 146B. Lower leaves, vegetative and flowering plants lower surface: Towards the margins, close to 158B; centers, close to 146B. Upper leaves, vegetative plants, upper surface: Close to 60B to 60D; towards the apex, close to 61A; random longitudinal stripes, close to 148A; venation, similar to leaf surface color. Upper leaves, vegetative plants, lower surface: Close to N77B; random longitudinal stripes, close to 146B; venation, similar to leaf surface color. Upper leaves, flowering plants, upper and lower surfaces: Close to 61A; venation, close to close to 61A.

Inflorescence description:

*Inflorescence form.*—Terminal flat-topped compact corymb located inside the leaf rosette; about 102 flowers develop per inflorescence.

*Flower longevity.*—Individual flowers last about one to two days on the plant; flowers persistent.

*Inflorescence length.*—About 5.5 cm.

*Inflorescence diameter.*—About 4.4 cm.

*Flower size.*—Length: About 3.7 cm. Diameter: About 7 mm.

*Fragrance.*—None detected.

*Flower buds.*—Length: About 3.2 cm. Diameter: About 4 mm. Shape: Elongated oblong. Color: Close to 91B.

*Petals.*—Quantity per flower: Three in a single whorl. Shape: Oblanceolate to elliptical. Apex: Mucronate. Base: Truncate. Margin: Entire. Length: About 2.5 cm. Width: About 5 mm Texture: Smooth, glabrous. Color: When opening, upper surface: Close to 91C. When opening, lower surface: Close to 91B. Fully opened, upper surface: Towards the apex, close to 92B; center, close to 92C; towards the base, close to NN155C. Fully opened, lower surface: Towards the apex, close to 92C; towards the base, close to NN155C.

*Flower bracts.*—Quantity per flower: One. Shape: Oblanceolate. Length: About 3.4 cm. Width: About 6 mm. Texture: Membraneous. Color: Close to NN155D.

*Sepals.*—Quantity per flower: Three in a single whorl. Shape: Lanceolate. Apex: Acuminate. Base: Truncate. Margin: Entire. Length: About 2.1 cm. Width: About 3 mm. Texture: Smooth, glabrous. Color, upper and lower surfaces: Towards the apex, close to 145D; towards the base, close to NN155C.

*Peduncles.*—Strength: Strong. Aspect: Typically erect. Length: About 4 cm. Diameter: About 1.8 cm. Texture: Smooth, glabrous. Color: Close to NN155A.

*Pedicels.*—Strength: Strong. Aspect: Typically erect to somewhat outward. Length: About 3 mm. Diameter: About 2 mm. Texture: Smooth, glabrous. Color: Close to NN155B.

*Stamens.*—Quantity per flower: About six. Filament length: About 1 cm. Filament color: Close to NN155C. Anther shape: Lanceolate. Anther length: About 4 mm. Anther color: Close to NN155A. Pollen amount: Moderate. Pollen color: Close to 155A.

*Pistils.*—Quantity per flower: One. Pistil length: About 2.5 cm. Stigma shape: Rounded. Stigma color: Close to NN155B. Style length: About 1.2 cm. Style color: Close to NN155B. Ovary color: Close to NN155D.

*Seed/fruit.*—Seed and fruit production have not been observed.

Temperature tolerance: Plants of the new *Neoregelia* have been observed to tolerate temperatures ranging from about 4° C. to about 37° C.

Interior & garden performance: Plants of the new *Neoregelia* have been observed to have good postproduction longevity under interior conditions and to have good garden performance.

Disease/pest resistance: Resistance to pathogens and pests common to *Neoregelia* has not been observed.

It is claimed:

1. A new and distinct *Neoregelia* plant named 'Autumn Rain' as illustrated and described.

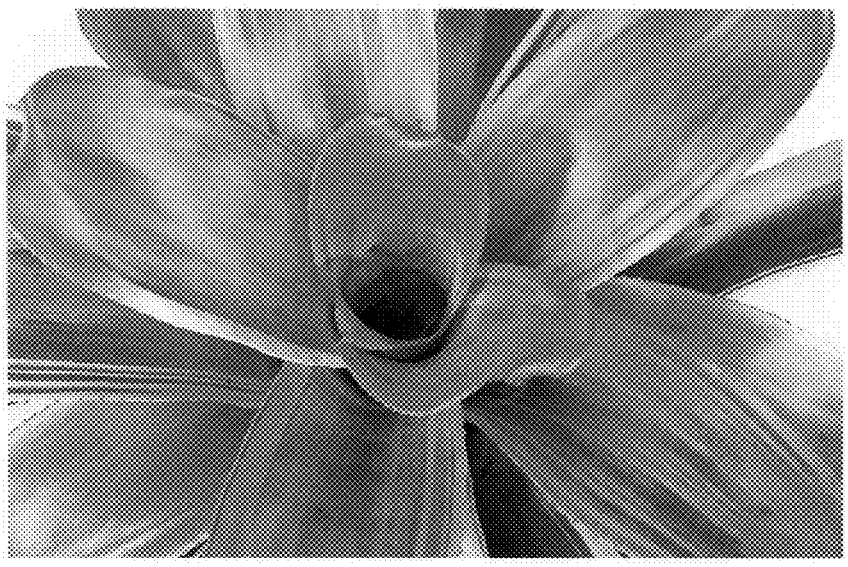
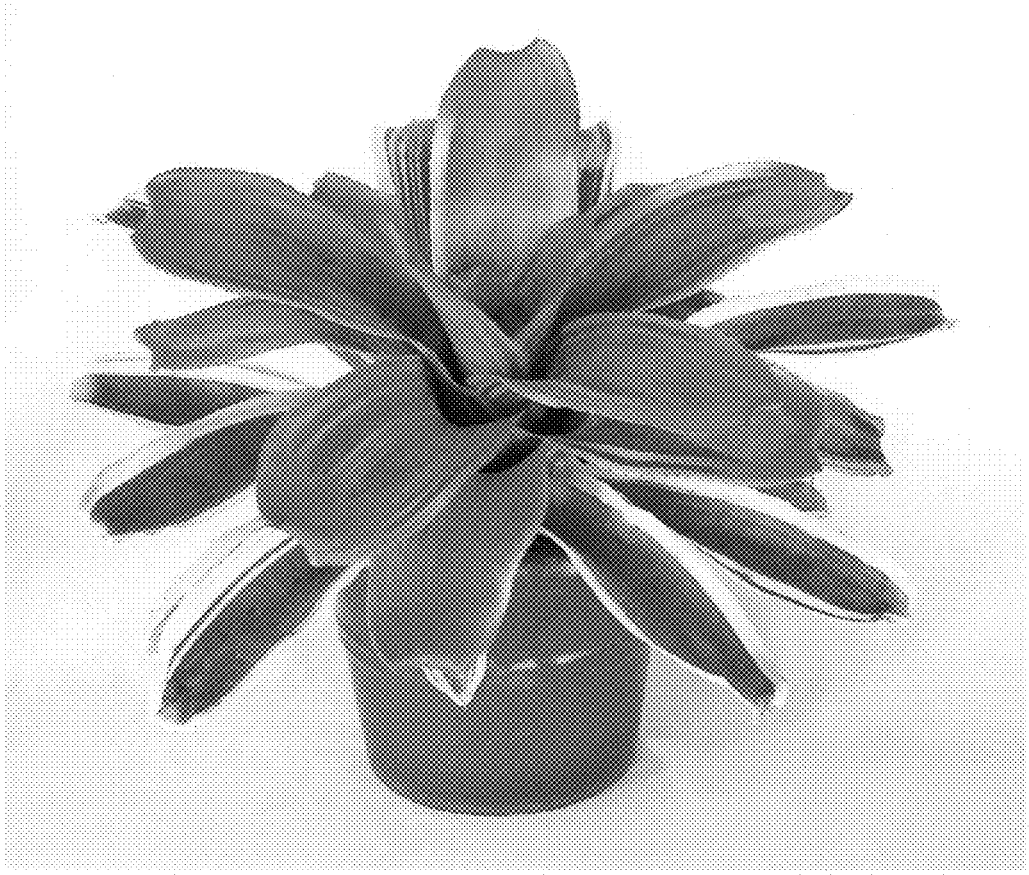

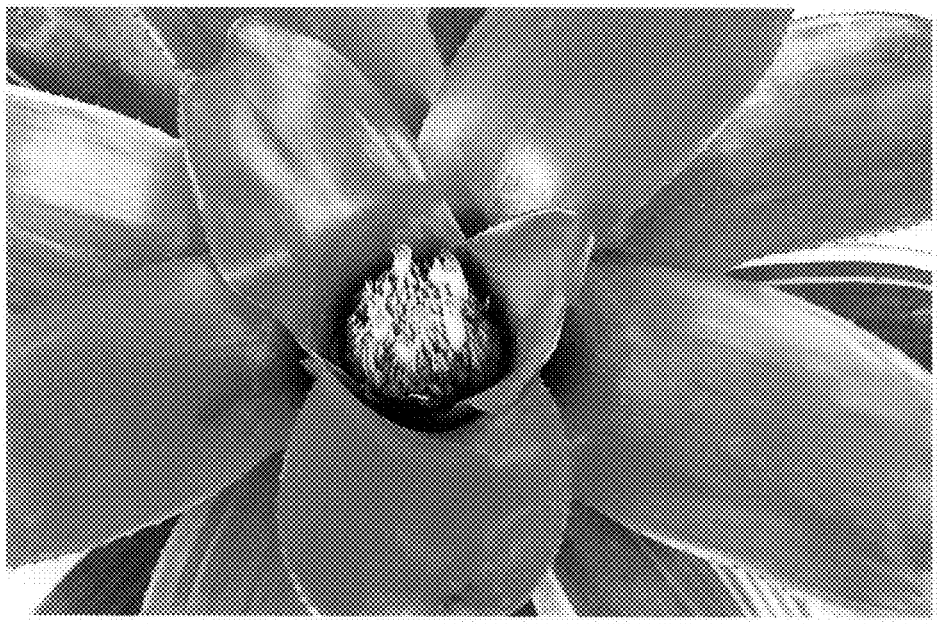
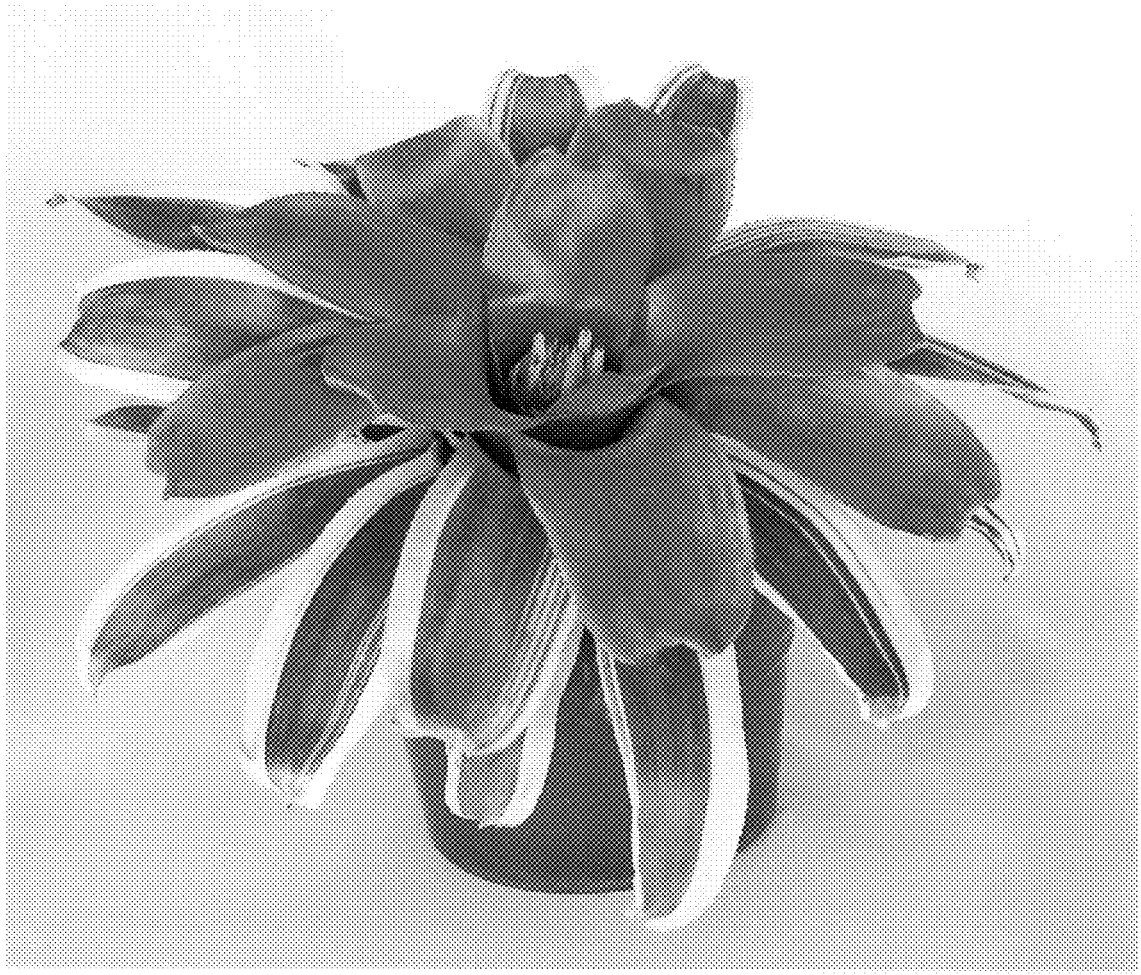

* * * * *